United States Patent [19]

Victor et al.

[11] Patent Number: 5,573,911
[45] Date of Patent: Nov. 12, 1996

[54] METHODS AND MATERIALS FOR DETECTING AUTOIMMUNE ANTIBODIES

[75] Inventors: Jacob Victor, Passaic, N.J.; Lisa M. Pieti, Norwalk, Conn.

[73] Assignee: Lifecodes Corp., Stamford, Conn.

[21] Appl. No.: 330,147

[22] Filed: Oct. 3, 1994

[51] Int. Cl.$^6$ ..................................... C12Q 1/68
[52] U.S. Cl. .............. 435/6; 435/7.1; 435/7.92; 435/973; 435/975; 436/501; 436/506; 436/508; 436/518; 436/531; 436/808; 436/809
[58] Field of Search ............... 427/2.11; 435/6, 435/7.1, 7.92, 973, 975; 436/501, 508, 506, 518, 531, 809, 808

[56] References Cited

U.S. PATENT DOCUMENTS

| | | | |
|---|---|---|---|
| 4,452,901 | 6/1984 | Gordon et al. | 436/506 |
| 4,681,853 | 7/1987 | Hardy et al. | 435/288 |
| 4,751,181 | 6/1988 | Keene | 436/506 X |
| 5,183,735 | 2/1993 | Lopez et al. | 435/6 |
| 5,292,662 | 3/1994 | Sandmeyer | 435/230.1 |
| 5,416,195 | 5/1995 | Camble et al. | 530/351 |

FOREIGN PATENT DOCUMENTS

| | | | |
|---|---|---|---|
| 0171150 | 2/1986 | European Pat. Off. | 435/973 X |
| 0205643 | 12/1986 | European Pat. Off. | 436/508 |
| 8808978 | 11/1988 | WIPO | 435/973 X |

OTHER PUBLICATIONS

Hames & Higgins (ed), Nucleic Hybridization: a practical approach (IRL Press Washington DC.) pp. 86–88 (1985).
Nehls et al, "Monoclonal antibody–based immunoassay for ... specific carcinogen—DNA adducts (O$^6$–alkyl guanine)," Carcinogenesis 11(1):81–87, 1990.
Schaltmann et al, "Identification . . . of the ecodysterone receptor in Drosophila melanagaster by photoaffinity labeling," Proc. Nat'l Acad. Sci. USA 79(1):6–10, 1982.
Craft, J., J. A. Hardin (1993) "Antinuclear Antibodies" Textbook of Rheumatology 4th Edition, pp. 164–187.
Francoeur, A.–M. (1989) "Anti–SM and Anti–U1–RNP Lupus Antibody Fine Specificities" Journal of Clinical Immunology 9(3):256–263.
Habets, W. J. et al. (1983) "Antibodies against distinct nuclear matrix proteins are chararteristic for mixed connective tissue disease" Clin. Exp. Immunol. 54:265–276.
Harmon, C. E. (1985) "Antinuclear Antibodies in Autoimmune Disease" Medical Clinics of North America 69(3):547–563.
McDuffie, F. C., J. J. Cavallaro (1987) "Antinuclear Antibody Tests" Laboratory Methods for the Detection of Antinuclear Antibodies–Immunology Series No. 14:1–5.
Reichlin, Morris (1993) "Antibodies to Defined Antigens in the Systemic Rheumatic Diseases" Bulletin on the Rheumatic Diseases 42(8):4–6.
Tan, Eng M. (1989) "Antinuclear Antibodies: Diagnostic Markers for Autoimmune Diseases and Probes for Cell Biology" Advances in Immunology 44:93–151.

Primary Examiner—Carol A. Spiegel
Attorney, Agent, or Firm—Saliwanchik & Saliwanchik

[57] ABSTRACT

The subject invention pertains to a method of binding proteins and double-stranded DNA to the same membrane matrix. The DNA bound to the membrane matrix remains in double-stranded form. The subject invention further concerns an assay procedure for detecting antibodies, such as autoimmune antibodies, in a biological sample that are immunoreactive with the proteins and double-stranded DNA attached to a membrane matrix. The subject invention provides a single assay system that allows for the determination of antinuclear antibody specificities which can be used to aid in the diagnosis and monitoring of autoimmune diseases.

22 Claims, 3 Drawing Sheets

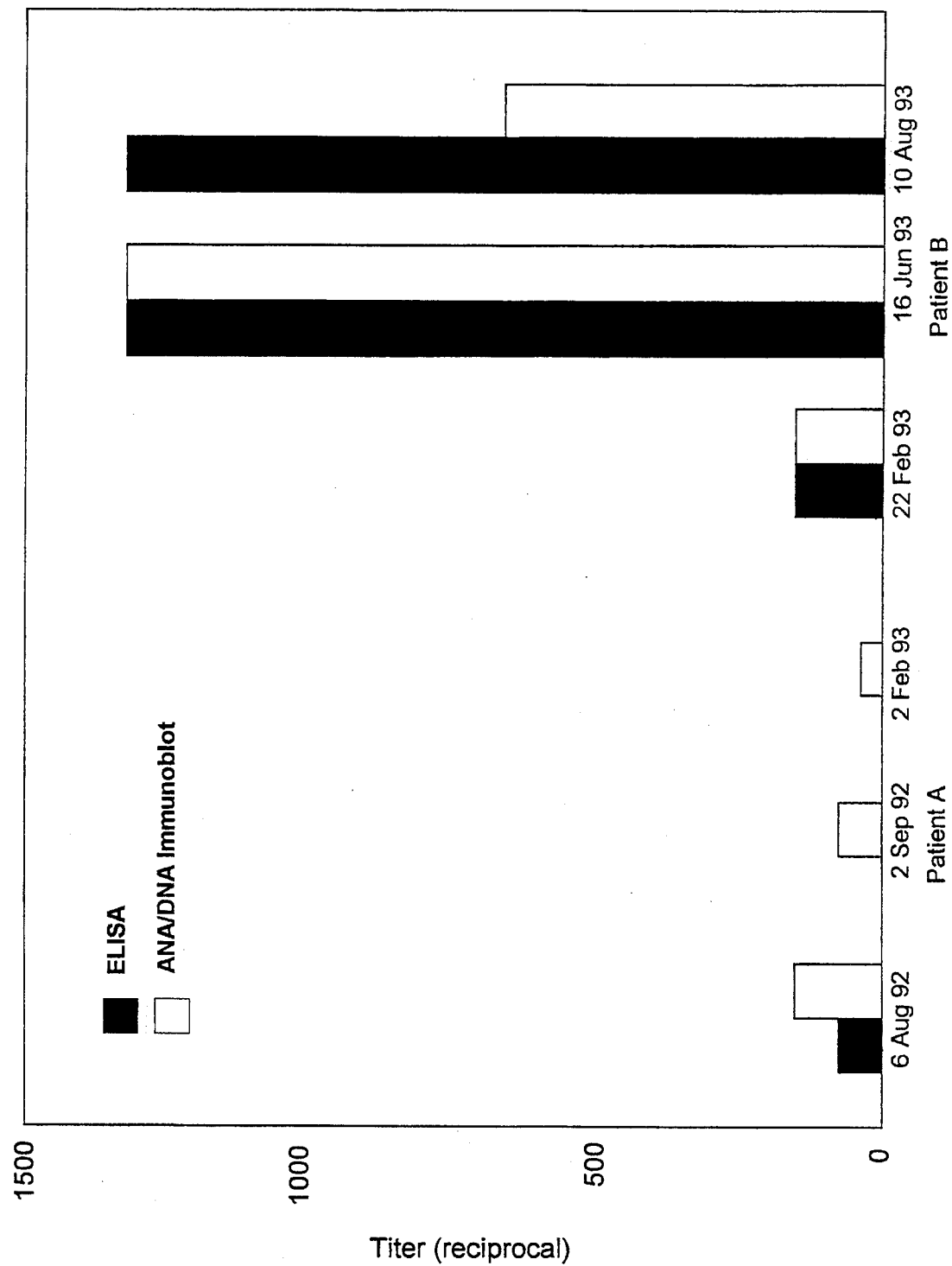

METHODS AND MATERIALS FOR DETECTING AUTOIMMUNE ANTIBODIES

BACKGROUND OF THE INVENTION

Autoimmune diseases are characterized by an abnormal immune response (involving either immune system cells or antibodies) directed against normal autologous (self) tissues. Autoimmune diseases afflict huge numbers of individuals throughout the world. A common characteristic of several autoimmune diseases is the presence of one or more types of antinuclear antibodies (ANA) in the bodily fluids of patients suffering from the disease. ANA's are autoantibodies directed against antigens in the nucleus and cytoplasm of a person's own cells. It is thought that these antibodies are responsible for the tissue injuries associated with autoimmune disease. Thus, the detection of ANA's can be of significant clinical or diagnostic value.

Antinuclear antibodies are prominent in the biological fluids of patients suffering from disorders such as Systemic Lupus Erythematosus (SLE), Systemic Sclerosis, Mixed Connective Tissue Disease (MCTD), and Sjogren's Syndrome (Tan, E. M., 1989; Craft et al., 1993). Immunofluorescent tests using cultured human cell substrates are useful in determining the presence of ANA's in human sera (McDuffie et al., 1987) but do not provide information regarding the specificity of the antibodies. The disease specificity of well characterized antinuclear antibodies is an important diagnostic aid when interpreted in conjunction with the patient's clinical condition. It can also be used to partition patients into clinical subsets, and in some instances the presence or titer of a specific ANA correlates with the patient's prognosis (Reichlin, M., 1993). Currently, the determination of antinuclear antibody specificity requires considerable additional testing.

The use of indirect immunofluorescence (IF) for the detection of ANA's dates back to 1957. This method is still the standard method used to screen for the presence of ANAs. Typically, the patient's serum is diluted 1:40 in a buffer solution and allowed to react with human cells that have been fixed on a glass slide. If there are antibodies in the patient's serum that are immunoreactive with antigen components associated with the cell, they will bind to the cells and form an antigen-antibody complex. After washing to remove any unbound material, the presence of antigen-antibody complexes are detected using an anti-human antibody labeled with a fluorescent indicator. The presence of a fluorescent signal is detected by viewing the cells under a fluorescent microscope. The fluorescent signal is transient and will disappear within a few hours or days. Sera which test positive for ANA can then be titered out to an endpoint (i.e., diluted 1:80, 1:160, etc., and reacted with cells as before until a fluorescent signal can no longer be detected under the microscope). Disease severity, and in some cases response to therapy, is measured by increases and decreases in the ANA titer in a patient.

In addition to determining the presence or absence of fluorescent signal, detection of certain patterns of fluorescence also provides useful information in diagnosing the specific disease that may be afflicting a patient. For example, a homogeneous fluorescent nuclear signal (i.e., an even staining of the entire nucleus within the cell) is indicative of SLE, while a speckled pattern (i.e., a fine or granular-appearing staining of the nucleus) can indicate Scleroderma, MCTD, Sjogren's Syndrome or Raynaud's Syndrome. The staining pattern is due to the reactivity of the patients' antibodies to specific nuclear or cytoplasmic components.

Unfortunately, the IF method is not strictly diagnostic of specific autoimmune disease because of the substantial overlap of the fluorescent patterns exhibited by a number of autoimmune diseases. Also, if the sample is not titered appropriately, masking of fluorescent patterns can occur. Furthermore, even if a pattern is seen that is suggestive of a specific autoimmune disease, extensive confirmatory testing with purified antigens such as Sm, Scl-70, Ro, La, RNP and double stranded DNA, using assays such as EIA's, immunodiffusion or hemagglutination is necessary before one can be reasonably sure of a diagnosis. Thus, IF is a tedious method which does not generate a permanent record, involves multiple assays, is time-consuming and labor intensive, and requires considerable expertise in the interpretation of results.

Western blots (immunoblots) have been used to detect certain antinuclear antibody specificities (Francoeur, A. M., 1989). The use of immunoblots for the detection of specific antigens recognized by ANAs provides several advantages over IF, immunodiffusion, immunoprecipitation and EIA methods including a) more complete information can be obtained about the number and molecular size of antigen, b) large antigen complexes are separated into their component antigenic polypeptides yielding very specific ANA reactivities, and c) immunoblotting is extremely sensitive and reproducible (Habets, W. J., et al., 1983). The antigen specificity of the antibody can be determined by comparison of the sample reactivity with control markers on the blot. However, the Western blot method cannot be used to detect antibodies that are immunoreactive with double-stranded DNA (dsDNA) since membranes that bind proteins do not bind DNA very well unless the transfer occurs under alkaline conditions; unfortunately, dsDNA becomes single stranded under these conditions. And since antibodies that bind single-stranded DNA (ssDNA) are present in both autoimmune and non-autoimmune diseases, a positive ssDNA immunoblot result has little clinical significance.

In contrast, the presence of antibodies to dsDNA has both diagnostic and therapeutic importance (Harmon, C. E., 1985). Moreover, the presence of antibodies to dsDNA and to an RNA-protein complex called Sm are serologic criteria used in the classification of SLE. These and other ANA specificities often appear concomitantly in SLE. In addition, increases or decreases in the end-point titer of ANA's to dsDNA is correlated with, and used in monitoring, the clinical progression of SLE in patients suffering from the disease.

The inability to test for both antibodies to protein and double-stranded DNA antigen using Western blotting techniques requires that a separate assay for antibodies to dsDNA be conducted. This results in additional cost and manpower, as well as increasing the risk of errors. Thus, there remains a need for a single assay that is sensitive, simple to use, and which provides specific ANA results to aid in diagnosis and monitoring of autoimmune diseases.

BRIEF SUMMARY OF THE INVENTION

The subject invention concerns a method for detecting antibodies to both specific proteins and to double-stranded DNA (dsDNA) in a single assay format. Specifically, the subject invention concerns a novel method for binding both dsDNA and target proteins on a membrane support. Advantageously, the DNA remains in double-stranded form after attachment to the membrane.

The subject invention further concerns a method for detecting the presence of anti-nuclear antibodies (ANA) in whole blood, plasma, serum or other bodily fluids of an animal or human. The subject invention can be used to aid in diagnosis, detect and/or monitor the presence of ANAs in various autoimmune diseases such as systemic lupus erythematosus (SLE).

The assay of the subject invention uses both dsDNA and target proteins bound to a membrane strip as described herein. The membrane strip is then reacted with a sample of the patient's serum or other bodily fluids. Antibodies present in the serum or fluids that react with the dsDNA or proteins can then be detected. The antigen specificity of the ANA's present can be distinguished by comparison of sample band position to positions of known marker antigens on the blot. The immunospecificity of the antibodies present in the sample can then be used to detect, monitor and/or aid in the clinical diagnosis of the disease afflicting a person.

BRIEF DESCRIPTION OF THE DRAWINGS

FIG. 3 shows a comparison between dsDNA ELISA and ANA immunoblot end-point titers of sera from two patients afflicted with autoimmune disease.

DETAILED DESCRIPTION OF THE INVENTION

Figure 1:
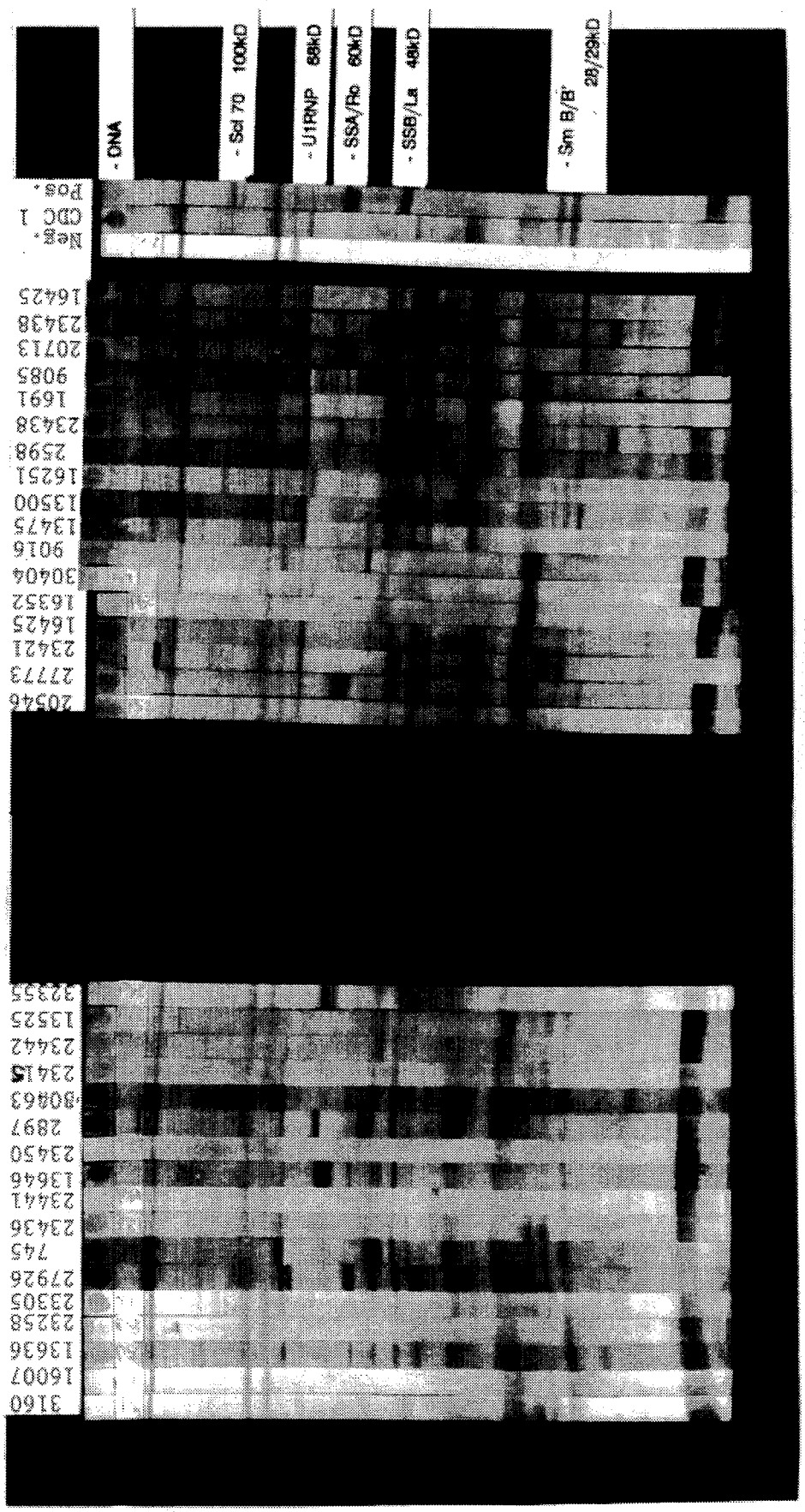
FIG. 1 shows an ANA immunoblot of serum samples from known, ill SLE clinic patients. The immunoblot strip had proteins from HEp2 cells along with double-stranded DNA bound to the membrane strip and were prepared as described herein. Positive and negative control samples are shown at the far right along with CDC reference 1. The location of common ANA specificities including Ro/SSA antigens are identified on the right.

The subject invention concerns a method for efficiently and reproducibly binding both proteins and dsDNA to a membrane support material. The ability to bind both proteins and dsDNA to the same membrane enables the skilled artisan to detect the presence of antibodies that are immunoreactive with the proteins or dsDNA in a single assay procedure. Heretofore, the skilled artisan has not been able to bind both proteins and dsDNA to the same membrane. Advantageously, the DNA remains in double-stranded form once it is attached to the membrane.

In one embodiment, protein antigens obtained from a lysate of cells or a cell line such as HEp2, HeLa, etc., are electrophoresed on a gel to separate the proteins according to their molecular weight (Laemmli, 1970). In another embodiment, purified and isolated protein antigens can also be used with the subject invention. The proteins can be obtained from natural sources or produced through standard genetic engineering techniques or peptide synthesis. The separated proteins are then electrophoretically transferred from the gel to a membrane matrix using standard Western blot procedures (Towbin et al., 1979). Preferably, the membrane is composed of polyvinylidene difluoride (PVDF). Optionally, the membrane can be composed of nitrocellulose or other materials known in the art.

After the proteins are transferred to the membrane, dsDNA is bound to the same membrane by blotting dsDNA onto the membrane at a location where no proteins were transferred. It is critical that the electrotransfer process be applied to the membrane prior to dsDNA blotting in order to achieve efficient dsDNA binding to the membrane. After drying and baking the membrane, the dsDNA is cross-linked to the membrane by exposure to UV light energy. Preferably, the UV light exposure is the equivalent of between about 100 to 400µ joules constant energy. More preferably, the UV exposure is the equivalent of about 300µ joules constant energy. The membrane can then be used to detect the presence of antibodies that react with the bound protein antigens and/or dsDNA in serum or other biological samples.

The subject invention further concerns a method for detecting autoimmune antibodies, such as anti-nuclear antibodies (ANA), in a biological fluid or sample. Membranes can be prepared that have dsDNA and protein antigens attached that are the targets of autoimmune antibodies. The resulting ANA-antigen complex can be detected using a variety of procedures and reagents that are known in the art. In one embodiment, the antibody-antigen complex can be detected using Protein A (or protein G) which binds almost irreversibly to human IgG. The Protein A can be labeled with a signal generating system such as biotin, which is detected using streptavidin coupled to an enzyme such as alkaline phosphatase. The presence of the ANA-antigen-Protein A-biotin-streptavidin-alkaline phosphatase complex is detected through the enzyme's reaction with a substrate that produces a visible band of color on the membrane. Typically, 5-bromo-4-chloro-3-indolyl-phosphate and nitroblue tetrazolium (BCIP/NBT) are used as the substrate for alkaline phosphatase.

Other antibody-antigen detection methods include the use of antibodies (of any species) that are reactive with the species of immunoglobulin being detected, examples of which include polyclonal anti-IgG or IgM, monoclonal anti-IgG or IgM, etc., and binding fragments thereof, such as Fab fragment. These anti-Ig antibodies may be labeled with a ligand (e.g. biotin), a hapten (e.g. dinitrophenol) or directly labeled with an enzyme (e.g., alkaline phosphatase, horseradish peroxidase, β-galactosidase, etc.) or a radioisotope ($^3$H, $^{125}$I, etc.) or any other detectable label known in the art.

If ANA are present in a sample, a distinct permanent "bar code" of bands appears directly on the membrane strip or can be indirectly produced from the membrane strip. Each band on the strip can be assigned to a specific protein-antibody complex. The prominence of the bands in the bar code can be correlated to the titer of the ANA present. Optionally, size marker bands can be placed on the membrane strip to aid in aligning the strips with any particular control strip. Advantageously, the subject invention has a higher sensitivity and lower background noise than the standard IF assay as evidenced by the detection of antibodies at higher titers in clinical samples when using the subject invention.

In one embodiment, the subject assay can be used to simultaneously detect antibodies to the following antigens: Sm B/B', Scl-70, SSA/Ro, SSB/La, U-1 RNP, Jo-1, CENP A and double-stranded DNA. The presence of specific combinations of these bands on the membrane strips aids in disease diagnosis and monitoring without having to determine the antibody titer in the sample. In addition, the "bar code" readout provides a permanent record of the assay results (particularly if the strip is photographed or digitized) while at the same time eliminating the difficult and time-consuming interpretation of fluorescent patterns.

The ANA assay of the subject invention can be completed manually in about 50 minutes. Interpretation of the bar codes can be performed visually or by image analysis. Both the front (assay) and back (interpretation) ends of the assay can be automated using standard equipment and electronics known in the art. The ability to consistently generate a highly reproducible colorimetric bar code allows the readout membrane to be used with simple reflectometers currently in use in doctors' offices for other strip type assays. Such bar code readers can give the physician a printout of a patient's autoimmune status upon analysis of the colorimetric pattern present on the membrane. The autoimmune assay of the subject invention can detect and titer ANA's more rapidly and with increased sensitivity than standard assays. In addition, the ability to detect and monitor specific diseases using the subject invention provides a significant advantage over the IF assay.

The subject invention further concerns a kit which contains certain reagents, controls and protein/DNA bound to membrane strips necessary for the rapid determination of ANA presence and specificity in human or animal sera, plasma, or other biological samples.

In one embodiment, the membrane strips of the subject invention are prepared by Western blotting a human cell line extract supplemented with additional proteins onto PVDF membranes. The dsDNA is then bound to the membrane after the proteins have been transferred by Western blotting. The human cell line HEp2 can be used as a source of antigens. The sample serum or plasma is incubated with the membrane strip and the ANAs present in the sample bind to specific antigens on the strip. The strips are washed to remove any unbound material and then incubated with biotinylated-Protein A, which binds to human IgG antibodies. The biotinylated-Protein A/human ANA bound to the strip is detected by using streptavidin conjugated with an enzyme such as alkaline phosphatase and a colorimetric enzyme substrate (NBT/BCIP is a substrate for alkaline phosphatase). A positive reaction, indicating the presence of ANA(s), can be seen visually as a colored band on the strip. ANA specificity is assigned when the position of the band(s) of the sample correlates to the same position on the ANA positive control strip profile.

The immunoreactive specificity of many antinuclear antibodies has been determined (Peters, J. B., 1991). These antibodies can be detected using the subject invention. These include, but are not limited to, ANA's to the following antigens: Scl-70, U-1 RNP, Ro/SSA, La/SSB, Jo-1, Sm, CENP A, and double-stranded DNA. A description of these specificities are shown in Table 1.

Following are examples which illustrate procedures, including the best mode, for practicing the invention. These examples should not be construed as limiting. All percentages are by weight.

EXAMPLE 1

Preparation of Protein/dsDNA Membrane

An extract of proteins from the HEp2 cell line (ATCC accession number: CCL-23) was prepared according to standard procedures known in the art. This HEp2 extract was supplemented with Ro/SSA antigen purified from bovine spleen and/or thymus (Immunovision, Springdale, Ark.). The antigen solution was placed in a boiling water bath for about 5 minutes and then run on a 15% SDS-polyacrylamide gel for about 16 hours at constant current (500 mA). The proteins present in the gel were then electrophoretically transferred to a PVDF membrane (Towbin, et al., 1979). Membranes were rinsed with distilled water and dried on blotting paper overnight at room temperature.

A suspension of native double-stranded DNA was prepared from the human K562 cell line (ATCC accession number: CCL-243) using standard procedures known in the art. The DNA suspension was mixed with S1 nuclease (1 unit S1 nuclease/1000 ng DNA) for 30 minutes at 37° Centigrade (C.) to digest any single-stranded DNA that might be present in the DNA suspension. Other nucleases that digest single-stranded DNA are contemplated for use in the subject invention. EDTA was added to a final concentration of about $10^{-3}$M. The DNA suspension was dot blotted (200 ng DNA per lane) on the unblocked top of the PVDF membranes to which the protein antigens had previously been electrotransferred. The DNA was allowed to air dry on the membrane for about 15 to 20 minutes, and then the membrane was baked at about 80° for about 30 minutes. After baking, the membrane antigens were cross-linked by exposure to the equivalent of 30μ joules constant energy of UV light.

As would be readily apparent to a person of ordinary skill in the art, the length of baking time and temperature can be more or less than the parameters illustrated above. Similarly, the skilled artisan could readily determine other UV light exposure levels which would bind the dsDNA to the mem-

TABLE 1

| Disease Specificity and Prevalence of ANAs | | | |
|---|---|---|---|
| Antigen | Disease Specificity | Prevalence of Antibody Detection | Molecular Weight (primary band in bold) |
| dsDNA | SLE | 75–90% | Dot at top of strip |
| Smith | SLE | 25–30% | B' 28 kD, B 27 kD, D 16 kD |
| U-1 RNP | SLE | 35–45% | 68 kD (triplet), |
|  | MCTD | 95–98% (high titer) | 34 kD, 22 kD |
| Ro/SSA | SLE | 25–35% | 60 kD, 52 kD |
|  | Sjögren's Syndrome | 50–60% |  |
| La/SSB | SLE | 10–21% | 48 kD, 43 kD |
|  | Sjögren's Syndrome | 40–50% |  |
| Scl 70 | Systemic Sclerosis | 20–25% | 100 kD |
| Centromere | CREST | 80–90% | 14 kD, 80 kD, 140 kD |
| Jo-1 | Myositis | 25–30% | 56 kD | brane without corrupting the "double-strandedness" of the DNA itself.

EXAMPLE 2

Detection of Antinuclear Antibodies

A membrane having the protein and double-stranded DNA attached was prepared as described in Example 1. Blood samples were obtained from patients and serum isolated according to standard procedures. The individual serum samples were then diluted 1:40 in an effective dilution reagent and added to the separate membranes and incubated for about 15 minutes at 37° C. After incubation the membranes were rinsed free of unbound antibody. An effective amount of biotinylated protein A solution was then added to the membrane and incubated for 15 minutes at 37° C. with mild agitation. The membrane was rinsed several times and then a solution of streptavidin alkaline-phosphatase was added onto the strip. The membrane was incubated for 15 minutes at 37° C. with mild agitation. The membrane is rinsed several times and a substrate solution of BCIP/NBT was added to the membrane. The substrate was allowed to react for about 5 minutes, or until distinct visible color bands appeared. The membrane was washed several times and then dried on absorbent paper. Membrane strips can be aligned using control molecular weight markers or other suitable markings on the membrane.

Using the antibody-antigen detection system described, a positive test for antibodies to a protein antigen results in the formation of a blue-violet color band. Samples positive for antibodies to double-stranded DNA will show a blue-violet dot where the DNA was dotted on the membrane. A positive control sample can include antibodies that react with the following antigens: double-stranded DNA, Scl-70 (100 kD), Ro/SSA (60 kD), Jo-1 (56 kD), La/SSB (48 kD), Sm B/B' (28,27 kD), and CENP A (14 kD) antigens.

Individual specificities of antinuclear antibodies can be determined by alignment of a sample band with a known reference band. For example, anti-Sm antibodies primarily yield a doublet band at 27–28 kD. If the sample membrane strip has a colored doublet band that aligns with the positive control reference band at 27–28 kD, then the Sm specificity can be assigned to that sample. Samples can demonstrate more than one antibody specificity and may have bands that do not align with control bands. Samples that show positive bands can be titered to determine the level of a particular antibody present in a sample. The end-point titer of a sample can be determined by making two-fold serial dilutions of all positive samples and controls. The end-point titer is the highest dilution that produces a detectable positive reaction.

An ANA immunoblot from an assay performed with the membrane strips as described herein and using sera from patients having SLE are shown in FIG. 1. Sera were diluted 1:40 for use in the assay. The colored bands represent antibody-antigen complexes detected using biotinylated Protein A and a strepatavidin alkaline-phosphatase detection system as described herein. Variations in the antigen reactivity of the antibodies present in sera from individual patients is evident. The majority of individuals show ANA's reactive with dsDNA and other antigens on the immunoblot.

Figure 2:
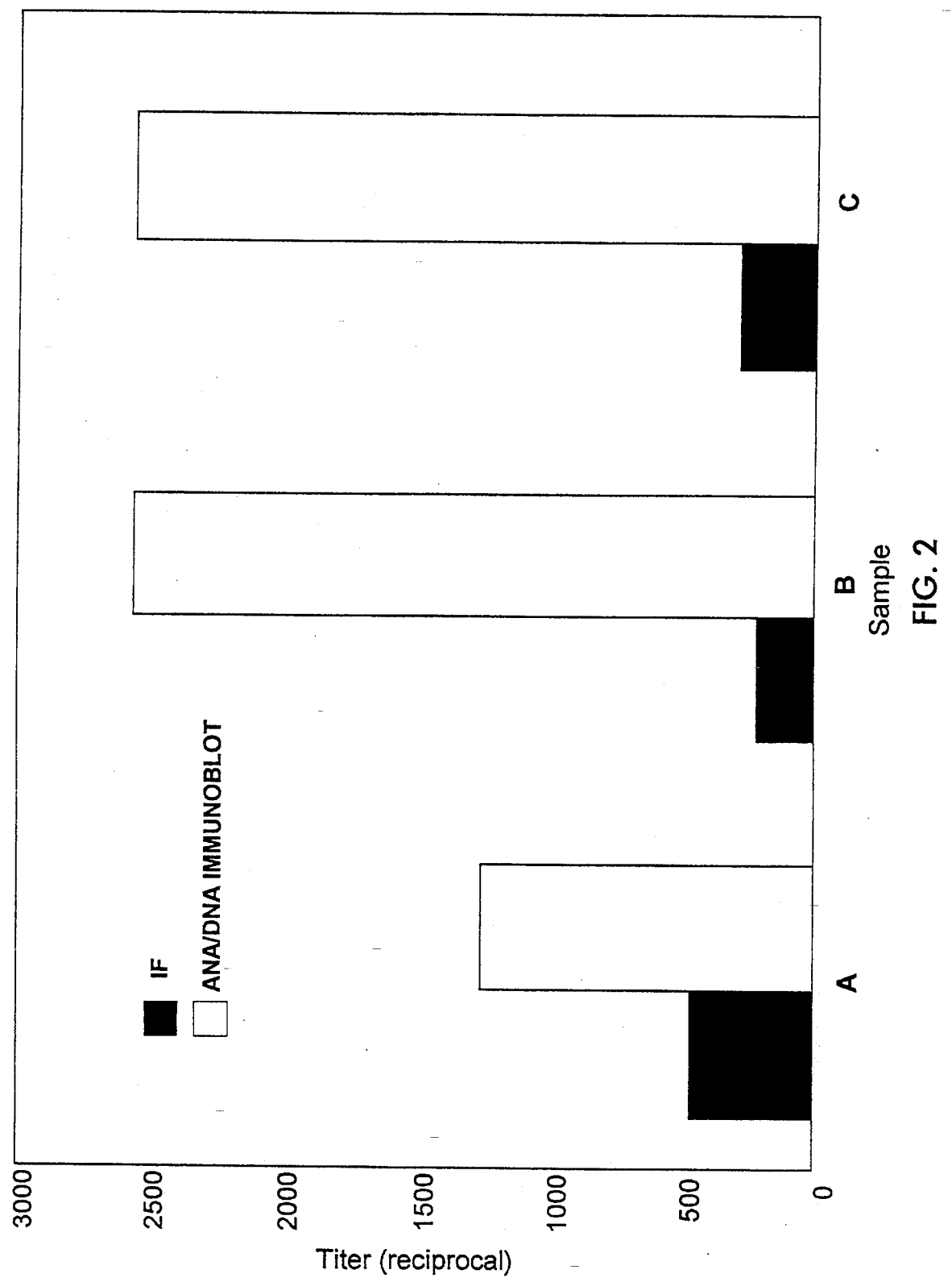
FIG. 2 shows a comparison between an immunofluorescence assay and ANA immunoblot end-point titers for three reference serum samples.

The assay of the subject invention is more sensitive than the standard IF assay for ANA as determined by measuring end-point titer for different sera samples. Sera from three different individuals suffering from autoimmune disease were assayed using IF under standard conditions and the ANA assay method of the subject invention as described in Example 2. End-point titers of sera in the subject assay were measured as the dilution of sera at which the last prominent band could be detected. FIG. 2 shows that the ANA assay of the subject invention was up to several-fold more sensitive than the IF assay.

The assay of the subject invention can also be used to monitor clinical disease progression over time in a patient suffering from autoimmune disease. The end-point titer of anti-dsDNA is directly correlated with the clinical progression of the disease. In a comparison between an ELISA dsDNA assay (Rubin, 1987) and the ANA immunoblot assay of the subject invention, performed as described in Example 2, a clear correlation between end-point titer changes in each assay was demonstrated. As shown in FIG. 3, the assay of the subject invention displayed a higher sensitivity of end-point titer detection, while changes in end-point titer mirrored ELISA endpoint titer movements over time. As is well known in the art, changes in the severity or clinical manifestation of many autoimmune diseases is directly correlated with end-point titer of anti-nuclear antibodies present in a patient's serum.

It should be understood that the examples and embodiments described herein are for illustrative purposes only and that various modifications or changes in light thereof will be suggested to persons skilled in the art and are to be included within the scope and purview of this application and the scope of the appended claims.

REFERENCES

Craft, J., and Hardin, J. (1993) Antinuclear and Anticytoplasmic Antibodies. *Textbook of Rheumatology* 4th edition, pp 164–187.

Francoeur, A. M. (1989) "Anti-Sm and Anti-U-1-RNP Lupus Antibody Fine Specificities," *J. Clin. Imm.* 9:256–263.

Habets, W. J., de Rooij, D. J. Salden, M. H., Verhagen, A. P., van Eekelen, C. A., van de Putte, L. B., and van Venrooij, W. J., (1983) "Antibodies Against Distinct Nuclear Matrix Proteins are Characteristic for Mixed Connective Tissue Disease," *Clin. Exp. Immunol.* 54:265–276.

Harmon, C. E. (1985) "Antinuclear Antibodies in Autoimmune Disease," *Medical Clinics of North America* 69:547–563.

Laemmli, U. K. (1970) "Cleavage of Structural Proteins During the Assembly of the Head of Bacteriophage T4," *Nature* 277:680–685.

McDuffie, F. C. and Cavallaro, J. J. (1987) Antinuclear Antibody Tests. "Laboratory methods for the detection of Antinuclear Antibodies" *Immunology Series* No. 14, pp 1–5.

Peters, J. B., (1991) *Use and Interpretation of Tests in Clinical Immunology,* 8th ed, Specialty Laboratories, Inc.

Reichlin, M. (1993) "Antibodies to Defined Antigens in the Systemic Rheumatic Diseases," *Bull. Rheum. Dis.* 42: 4–6.

Rubin, R. L. (1987) "Enzyme-linked Immunosorbent Assay for Anti-dsDNA and Antihistone Antibodies," *Laboratory Methods for the Detection of Antinuclear Antibodies Immunology* Series No. 14, U.S. Department of Health and Human Services, Center for Disease Control, 81–102.

Tan, E. M. (1989) "Antinuclear Antibodies: Diagnostic Markers for Autoimmune Diseases and Probes for Cell Biology," *Advances in Immunology* Vol 44: pp 93–151.

Towbin, H., Staehelin, T., and Gordon, J., (1979) "Electrophoretic Transfer of Proteins from Polyacrylamide Gels to Nitrocellulose Sheets: Procedure and Some Applications," *Proc. Natl. Acad. Sci. U.S.A.* 76: 4350–4354.

We claim:

1. A method for co-immobilizing double-stranded DNA and at least one preselected protein to separate and discrete areas on a single membrane matrix, wherein said membrane matrix comprises a matrix composition other than nitrocellulose, said method comprising the sequential steps of:

(a) immobilizing said at least one preselected protein to a first discrete area on said membrane matrix by electrophoretically transferring an electropherogram of a first protein solution containing said at least one preselected protein to said membrane matrix, wherein said at least one preselected protein is identifiable by its location on said electropherogram;

(b) applying a second solution comprising said double-stranded DNA onto a second discrete area on an end of said membrane matrix that does not have transferred proteins thereon, wherein said second solution does not contain detectable amounts of single-stranded DNA;

(c) baking said membrane matrix for an effective period of time and at a sufficient temperature to fix said double-stranded DNA to said membrane matrix; and (d) exposing said membrane matrix to an effective amount of UV light to covalently bind said double-stranded DNA to said membrane matrix, wherein said double-stranded DNA remains double-stranded during and after said exposure to said UV light.

2. The method, according to claim 1, wherein said membrane matrix is baked at about 80° C. for about 30 minutes.

3. The method, according to claim 1, wherein said membrane matrix is exposed to an equivalent of between about 100 and 400µ joules constant energy UV light.

4. The method, according to claim 1, wherein said membrane matrix is exposed to an equivalent of about 300µ joules of constant energy UV light.

5. The method, according to claim 1, wherein said membrane matrix is selected from the group consisting of nylon, and polyvinylidene difluoride (PVDF).

6. The method, according to claim 1, wherein said second solution is pre-treated to eliminate any single-stranded DNA present in said second solution prior to application to said membrane matrix.

7. The method, according to claim 6, wherein said second solution is pre-treated with an enzyme capable of digesting single-stranded DNA.

8. The method, according to claim 7, wherein said enzyme is S1 nuclease.

9. A membrane matrix comprising at least one preselected protein and double-stranded DNA co-immobilized on separate and discrete areas on said membrane matrix, wherein said membrane matrix comprises a matrix composition other than nitrocellulose, and wherein said at least one preselected protein and said double-stranded DNA are co-immobilized on said membrane matrix according to the method of claim 1.

10. The membrane matrix, according to claim 9, wherein said membrane matrix is selected from the group consisting of polyvinylidene difluoride (PVDF) and nylon.

11. A method for aiding in diagnosing and/or monitoring of an autoimmune disease in an individual comprising the steps of:

(a) contacting the membrane matrix of claim 9 with a biological sample from said individual; and (b) detecting any immune complexes that form between any antinuclear antibodies present in said biological sample and said double-stranded DNA and/or said at least one preselected protein immobilized on said membrane matrix to indicate the presence or amount of said antinuclear antibodies in said biological sample, wherein the presence or amount of said antinuclear antibodies aids in the diagnosis and/or monitoring of said autoimmune disease.

12. The method, according to claim 11, wherein said biological sample is selected from the group consisting of whole blood, plasma, and serum.

13. The method, according to claim 11, wherein said membrane matrix is selected from the group consisting of nylon and polyvinylidene difluoride (PVDF).

14. The method, according to claim 11, wherein said immune complexes are detected using an antibody-specific reagent which specifically binds to said antinuclear antibodies.

15. The method, according to claim 14, wherein said antibody-specific reagent is selected from the group consisting of Protein A, Protein G, monoclonal anti-immunoglobulin antibody and polyclonal anti-immunoglobulin antibody.

16. The method, according to claim 14, which further comprises contacting said antibody-specific reagent with a second reagent which binds to said antibody-specific reagent, wherein said second reagent is labeled with a single generating molecule capable of generating a detectable signal, and detecting said signal generated by said second reagent bound to said antibody-specific reagent, wherein the detection of said signal indicates the presence or amount of said antinuclear antibodies in said biological sample.

17. The method, according to claim 16, wherein said signal generating molecule is selected from the group consisting of radioisotopes, enzymes and fluorescent molecules.

18. The method, according to claim 14, wherein said antibody-specific reagent is labeled with a signal generating molecule capable of generating a detectable signal, wherein detection of said signal indicates the presence or amount of said antinuclear antibodies in said biological sample.

19. The method, according to claim 18, wherein said signal generating molecule is selected from the group consisting of radioisotopes, enzymes and fluorescent molecules.

20. A kit for aiding in diagnosing and/or monitoring of an autoimmune disease, comprising in one or more containers:

(a) the membrane matrix of claim 9; and (b) a positive or negative antinuclear antibody control reagent.

21. The kit, according to claim 20, further comprising:

(c) buffers for washing said membrane matrix; and (d) reagents for detecting and visualizing antibodies.

22. The kit, according to claim 21, wherein said reagents for detecting and visualizing antibodies comprise:

d)(i) an antibody-specific reagent which specifically binds to said antibodies; and, d)(ii) means for detecting said antibody-specific reagent either directly or indirectly.

* * * * *

UNITED STATES PATENT AND TRADEMARK OFFICE
CERTIFICATE OF CORRECTION

PATENT NO. : 5,573,911
DATED : November 12, 1996
INVENTOR(S) : Jacob Victor and Lisa M. Pieti It is certified that error appears in the above-indentified patent and that said Letters Patent is hereby corrected as shown below:

Column 5, Table 1 should be shown as:

| Table 1. Disease Specificity and Prevalence of ANAs ||||
|---|---|---|---|
| Antigen | Disease Specificity | Prevalence of Antibody Detection | Molecular Weight (primary band in bold) |
| dsDNA | SLE | 75 - 90 % | Dot at top of strip |
| Smith | SLE | 25 - 30 % | B' 28 kD, B 27 kD, D 16 kD |
| U-1 RNP | SLE<br>MCTD | 35 - 45 %<br>95 - 98 % (high titer) | 68 kD (triplet), 34 kD, 22 kD |
| Ro/SSA | SLE<br>Sjögren's Syndrome | 25 - 35 %<br>50 - 60 % | 60 kD, 52 kD |
| La/SSB | SLE<br>Sjögren's Syndrome | 10 - 21 %<br>40 - 50 % | 48 kD, 43 kD |
| Scl 70 | Systemic Sclerosis | 20 - 25 % | 100 kD |
| Centromere | CREST | 80 - 90 % | 14 kD, 80 kD, 140 kD |
| Jo-1 | Myositis | 25 - 30 % | 56 kD |

UNITED STATES PATENT AND TRADEMARK OFFICE
CERTIFICATE OF CORRECTION

PATENT NO. : 5,573,911
DATED : November 12, 1996
INVENTOR(S) : Jacob Victor and Lisa M. Pieti It is certified that error appears in the above-indentified patent and that said Letters Patent is hereby corrected as shown below:

Column 6, Line 39: "30 $\mu$ joules" should read --300 $\mu$ joules--.

Column 6, Line 40: "fight" should read --light--.

Signed and Sealed this

Thirteenth Day of May, 1997

Attest:

BRUCE LEHMAN

Attesting Officer   Commissioner of Patents and Trademarks